(12) United States Patent
Sivertsen et al.

(10) Patent No.: US 12,161,461 B2
(45) Date of Patent: *Dec. 10, 2024

(54) SYSTEM, SENSOR AND METHOD FOR MONITORING HEALTH RELATED ASPECTS OF A PATIENT

(71) Applicant: OMNISCIENT MEDICAL AS, Oslo (NO)

(72) Inventors: Reinert Sivertsen, Oslo (NO); Henriette Hårseide Bjørn, Lysaker (NO)

(73) Assignee: OMNISCIENT MEDICAL AS, Oslo (NO)

( * ) Notice: Subject to any disclaimer, the term of this patent is extended or adjusted under 35 U.S.C. 154(b) by 0 days.

This patent is subject to a terminal disclaimer.

(21) Appl. No.: 18/536,625

(22) Filed: Dec. 12, 2023

(65) Prior Publication Data
US 2024/0099607 A1     Mar. 28, 2024

Related U.S. Application Data

(62) Division of application No. 16/765,730, filed as application No. PCT/NO2018/050289 on Nov. 21, 2018, now Pat. No. 11,883,157.

(Continued)

(51) Int. Cl.
*A61B 5/11*     (2006.01)
*A61B 5/00*     (2006.01)
(Continued)

(52) U.S. Cl.
CPC ........... *A61B 5/1115* (2013.01); *A61B 5/1117* (2013.01); *A61B 5/4094* (2013.01);
(Continued)

(58) Field of Classification Search
CPC ..... A61B 5/115; A61B 5/1117; A61B 5/4094; A61B 5/7264; A61B 5/7275; A61B 5/746;
(Continued)

(56) References Cited

U.S. PATENT DOCUMENTS 11,883,157 B2 *  1/2024  Sivertsen ............. A61B 5/1117
2009/0048500 A1   2/2009  Corn
(Continued)

FOREIGN PATENT DOCUMENTS

| WO | WO 2016/174662 A1 | 11/2016 |
| WO | WO 2018/037288 A2 | 3/2018 |
| WO | WO 2018/136402 A2 | 7/2018 |

OTHER PUBLICATIONS

English translation of Japanese Office Action for Japanese Application No. 2020-545214, dated Aug. 8, 2022.
(Continued)

*Primary Examiner* — Curtis B Odom
(74) *Attorney, Agent, or Firm* — Birch, Stewart, Kolasch & Birch, LLP

(57) ABSTRACT

A method is provided for detecting an undesirable event or condition in a patient. The method may comprise receiving a first input signal from an UWB radar configured to monitor an environment occupied by the patient and including information representative of the patient's motion. Data derived from the first input signal is processed using a pattern recognition model to detect and classify patterns in the data derived from the first input signal as indicative or predictive of an undesirable event or condition involving the patient. When a pattern is classified as indicative or predictive of an undesirable event or condition in the patient an alarm is issued. A log of data derived from the first input signal and associated with a detection of a pattern classified as indicative or predictive of an undesirable event enables further (Continued)

machine learning in order to create an updated pattern recognition model based on individual patient behavior.

20 Claims, 7 Drawing Sheets

Related U.S. Application Data

(60) Provisional application No. 62/589,431, filed on Nov. 21, 2017.

(51) Int. Cl.
- *G01S 13/66* (2006.01)
- *G06N 20/00* (2019.01)
- *G16H 40/20* (2018.01)
- *G16H 40/67* (2018.01)

(52) U.S. Cl.
CPC .......... *A61B 5/7264* (2013.01); *A61B 5/7275* (2013.01); *A61B 5/746* (2013.01); *A61B 5/747* (2013.01); *G01S 13/66* (2013.01); *G06N 20/00* (2019.01); *G16H 40/20* (2018.01); *G16H 40/67* (2018.01); *A61B 2562/02* (2013.01)

(58) Field of Classification Search
CPC ........ A61B 5/747; G16H 40/67; G16H 40/20; G06N 20/00; G01S 13/66
See application file for complete search history.

(56) References Cited

U.S. PATENT DOCUMENTS

| | | |
|---|---|---|
| 2014/0163343 A1 | 6/2014 | Heneghan et al. |
| 2016/0345832 A1 | 12/2016 | Pavagada Nagaraja et al. |
| 2016/0377705 A1 | 12/2016 | Zack et al. |
| 2017/0005958 A1 | 1/2017 | Frenkel et al. |

OTHER PUBLICATIONS

Son et al. "Diabetic patient care using home user activity recognition", 2013 International Conference On ICT Convergence (ICTC), IEEE, Oct. 14, 2013, pp. 191-196.

* cited by examiner

SYSTEM, SENSOR AND METHOD FOR MONITORING HEALTH RELATED ASPECTS OF A PATIENT

This application is a Divisional of copending application Ser. No. 16/765,730 filed May 20, 2020, which is the National Phase of PCT International Application No. PCT/NO2018/050289 filed on Nov. 21, 2018, which claims priority under 35 U.S.C. 119(e) to U.S. Provisional Application No. 62/589,431, filed on Nov. 21, 2017, all of which are hereby expressly incorporated by reference into the present application.

TECHNICAL FIELD

The present disclosure describes a system and a sensor based on UWB (ultra-wideband RF) technology for sensing motion, as well as associated methods. In particular the disclosure describes a sensor, a system and methods for sensing motion and, in some embodiments, adapting to the patient's normal behavior and condition (i.e. learn what is normal for the patient) to better sense when something is wrong, and to track the patients changes over time for valuable insight, and in order to find patterns in the patient's health condition from the data provided and recorded.

BACKGROUND

It is desirable to monitor health related aspects of patients in order to be able to detect undesirable conditions at an early stage. This can include detecting symptoms that are indicative of the onset of such a condition as well as accidents such as falls. Many systems that address these issues include sensors that have to be attached to the patient resulting in discomfort or reduced ability to move freely, or sensors that work at a distance are inaccurate, they are unable to detect certain parameters, or they are associated with privacy issues.

Global life expectancy has increased dramatically over the past several decades. Due to advancements in technology and increased consciousness about personal hygiene and nutrition, people are living longer and healthier. As a consequence, we have a rapidly aging society where the prevailing home care model, as well as nursing homes, are failing to meet the growing population of elderly that requires care. The gap between available nurses and the needs of residents at nursing homes are growing at an increasing speed. Based on projections compiled by journal of nursing management, the shortage is expected to reach 200,000 nurses by the year 2030 for Germany alone. For the European Union, this amounts to 600,000 nurses, and for the United States—800 000, by the year 2020. For Long-term care facilities, and nursing homes in particular, the pressure on the nurses is rising as they already face nurse shortage, and the lack of care specialists results in longer work hours and is substantially lowering the quality of care for elderly. Additionally, several studies conducted in UK and Ireland as well as the present inventors' our own research, revealed other severe issues with nighttime caretaking. From the residents' point of view, main issues include the sleep disturbance caused by constant room entry for check-ups. With fewer skilled workers health deterioration detection can be delayed. During night time there can go hours between each check-up, which entails that severe falls and acute illnesses can take hours to detect, causing unnecessary harm and suffering. From the nurses' point of view, the main issues with night-work includes huge workload, health problems caused by night shift work, as well as employment of unskilled labor upon emergencies.

According to WHO, 50 million people worldwide have epilepsy and 30% of the patients with epilepsy do not have control over their condition, and are therefore in need of constant care and monitoring. This is especially true during the night, when seizures happen unsupervised. Insufficient treatment of epilepsy is related to increased probability of injury and SUDEP (Sudden Unsuspected Death in Epilepsy)—a situation where a person with epilepsy dies without evident cause.

We develop an innovative night monitoring- and decision support-system, for the prevention of missed events of health deterioration, early sickness detection, respiration distress, epileptic/non-epileptic seizure-prevention, detection, classification and trend monitoring and fall detection during the night or when in bed. Our invention will contribute to remedy unnecessary hospitalizations, assist the care of elderly, chronically ill and other persons in need of health monitoring to provide superior personalized care. Our solution will detect abnormal events, through the use of a sensor combined with machine learning, and promptly alert care givers at nursing homes and care facilities or relatives at home.

The most important method of seizure related screening and monitoring is the EEG (electrocochleogram), which measures the electrical signal activity in the brain using electrodes attached to the scalp of a patient/person. The problem with EEG is that it requires trained health personnel for attachment on patient/person and is very obtrusive for the patient/person wearing the setup. EEG is thus, in most cases, only used in hospital environments. Other existing types of technology targeting persons with epilepsy are wearables, cameras and mattress sensors. Wearables are obtrusive to wear for the user, cameras have privacy issue as well as not being able to see through thick bed blankets and mattress sensors are dependent on mattress thickness and has a short lifespan due to mechanical wear. Cameras are not able to detect vital signs, which may be vital in detecting seizures. A research article from 2016 "Automated seizure detection systems and their effectiveness for each type of seizure" by A. Ulate-Campos, F. Coughlin, M. Gaínza-Lein, L Sánchez Fernández, P. L. Pearl T. Loddenkemper, published in Seizure volume 40, 2016, analyzed available devices on the market and found that there is a need for devices that can unobtrusively measure several vital signs to cover different kinds of seizures and recommend the use of non-wearables due to wearables being obtrusive to use during the nighttime, especially for children. According to this article, abundant evidence confirms that patient specific algorithms are crucial for achieving accurate detection devices.

Solutions for continuous measurement of health parameters and falls of elderly patients, specifically designed for nursing homes and long term care facilities, are very limited. The existing solutions are mainly based on wearables, mattress sensors or cameras.

Wearable devices are the most commonly used technology, but they are uncomfortable for users, and have limited accuracy and short battery life. Moreover, this technology can be used incorrectly particularly by elderly patients with dementia who may also take off wearable devices and forget to put them back on, something which is highly likely to occur.

With respect to contactless device, such as mattress sensors, camera technologies and floor mats, their inconvenience and accuracy are the main issues. Specifically considering the mattress sensors, the patient needs to be placed directly on or above the sensor, since it does not cover the entire bed, and there are several constrains particularly regarding the mattress thickness and sensor's repositioning. Wearables and mattress sensors are also subject to physical wear, which limits device lifetime.

Moreover, these devices lack sufficient individual configuration, as their configurations, settings and limits are similar to one-size-fits all, with the configuration options limited to defining threshold values for detection and alarms. No real personalization is available in the current technology on the market. It is therefore a need for equipment capable of performing unobtrusive monitoring of falls, alerting caregivers when falls do happen, analyze falls and contribute to prevention of falls through personalized analysis of movement behavior.

Existing solutions lack the ability to adapt to the user and provide historical data analysis to remedy unnecessary health deterioration and hospitalizations. They also lack the ability to incorporate data provided by third party sensors.

SUMMARY OF THE DISCLOSURE

The present invention seeks to mitigate at least some of the shortcomings of the systems that are already available.

According to one aspect of the invention, a method is provided for detecting an undesirable event or condition in a patient. The method includes receiving a first input signal from an UWB radar configured to monitor an environment occupied by the patient and including information representative of the patient's motion. The received signal may be pre-processed, and the data derived from the first input signal may then be processed using a pattern recognition model to detect and classify patterns in the data derived from the first input signal as indicative or predictive of an undesirable event or condition involving the patient. When a detected pattern is classified as indicative or predictive of an undesirable event or condition in the patient, an alarm is issued. A log of data derived from the first input signal and associated with a detection of a pattern classified as indicative or predictive of an undesirable event is created and at intervals, the log may be processed using a machine-learning algorithm to create an updated pattern recognition model.

According to some embodiments, the pattern recognition model is a pre-trained model enabling detection of abnormal behavior based on an input signal received from an UWB radar. This original pattern recognition model may have been generated using the same or a similar machine learning algorithm, but on already existing data obtained from similar environments and similar patients, but the update based on machine learning from data relating to the specific patient enables the system to adapt to individual patient's behavior.

In some embodiments, the trained model is specifically trained to enable detection of at least one of an onset of an epileptic seizure and a fall. Other events and conditions may also be trained for.

According to some embodiments, the log is not only processed to learn to adapt to the specific patient, but also to track long term changes in behavior in order to detect changes over time and capture changes in patient medical condition.

The invention may be further adapted by adding additional sensors. In some embodiments, the method further includes receiving a second input signal from at least one additional sensor and including the second input signal with the first input signal when the first input signal is processed and monitored.

The at least one additional sensor may be chosen from the group consisting of: a microphone, a thermometer, a photodetector, an air quality sensor, an air humidity sensor, VOC-sensor, a barometer, and a heart rate sensor.

In some embodiments of the invention, the first input signal further includes information representative of the patient's vital signs.

In some embodiments, the receiving and processing using a pattern recognition model is performed in a local device containing or connected to the UWB radar.

In some embodiments, the processing of said log using a machine-learning algorithm to create an updated pattern recognition model is performed by a machine-learning module in a local device containing or connected to said UWB radar.

As an alternative to or in addition to local execution of the machine learning algorithm, processing of the log using a machine learning algorithm to create an updated pattern recognition model may also be performed by transmitting log data to a server based cloud service over a wide area network and receiving the updated pattern recognition model from the server based cloud service in response. Machine learning in more than one location (locally and in the cloud) may be used in order to maintain several pattern recognition models each related to recognition of patterns related to different classes of behavior, conditions or events, different combinations of sensor data, related to short term detection of events vs. long term monitoring of health status, or combinations of some or all of these.

The information representative of the patient's motion may include information representative of random body movement. This allows the method to train the pattern recognition model to detect a wide range of behaviors or motions relating to a wide range of events, conditions, seizures and other situations.

In some embodiments, the method further includes, upon detection of abnormal behavior, classifying the abnormal behavior as indicative as a specific event or prediction, selecting a message to be representative of or associated with the alarm based on the result of the classifying, and transmitting or publishing the message to an intended recipient.

According to another aspect of the invention, a device is provided for monitoring a patient in order to detect undesirable events or conditions. The device may include a processor configured to receive sensor data including a first input signal from an UWB radar, a memory, a pattern recognition model stored in the memory and enabling the processor to perform pattern recognition processing of data derived from the first input signal and to detect and classify patterns in the data derived from the first input signal as indicative or predictive of an undesirable event or condition in a patient within the a field of view of the UWB radar, and a communication interface. The processor may be configured to transmit an alarm message over the communication interface when a pattern is classified as indicative or predictive of an undesirable event or condition in the patient, create a log of data derived from the first input signal and associated with a detection of a pattern classified as indicative or predictive of an undesirable event, and process, at intervals, the log using a machine learning algorithm to create an updated pattern recognition model.

According to some embodiments the device may further comprise a machine learning module, and the processor may be configured to create the log by storing a segment of the data derived from the first input signal along with a result of classification of a pattern included in the segment in the memory, and to process the log using the machine learning module.

In various embodiments, a device according to the invention the machine-learning module may be installed as a software module in the memory, or it may be installed in the device as a separate hardware component controlled by the processor.

In some embodiments the processor is configured to create the log by transmitting a segment of the data derived from the first input signal along with a result of classification of a pattern included in the segment to a cloud service for inclusion in a log maintained by the cloud service, and to process the log using a machine learning algorithm by transmitting log data to a server based cloud service over a wide area network using the communication interface and receiving the updated pattern recognition model from the server based cloud service in response.

DETAILED DESCRIPTION

Figure 1:
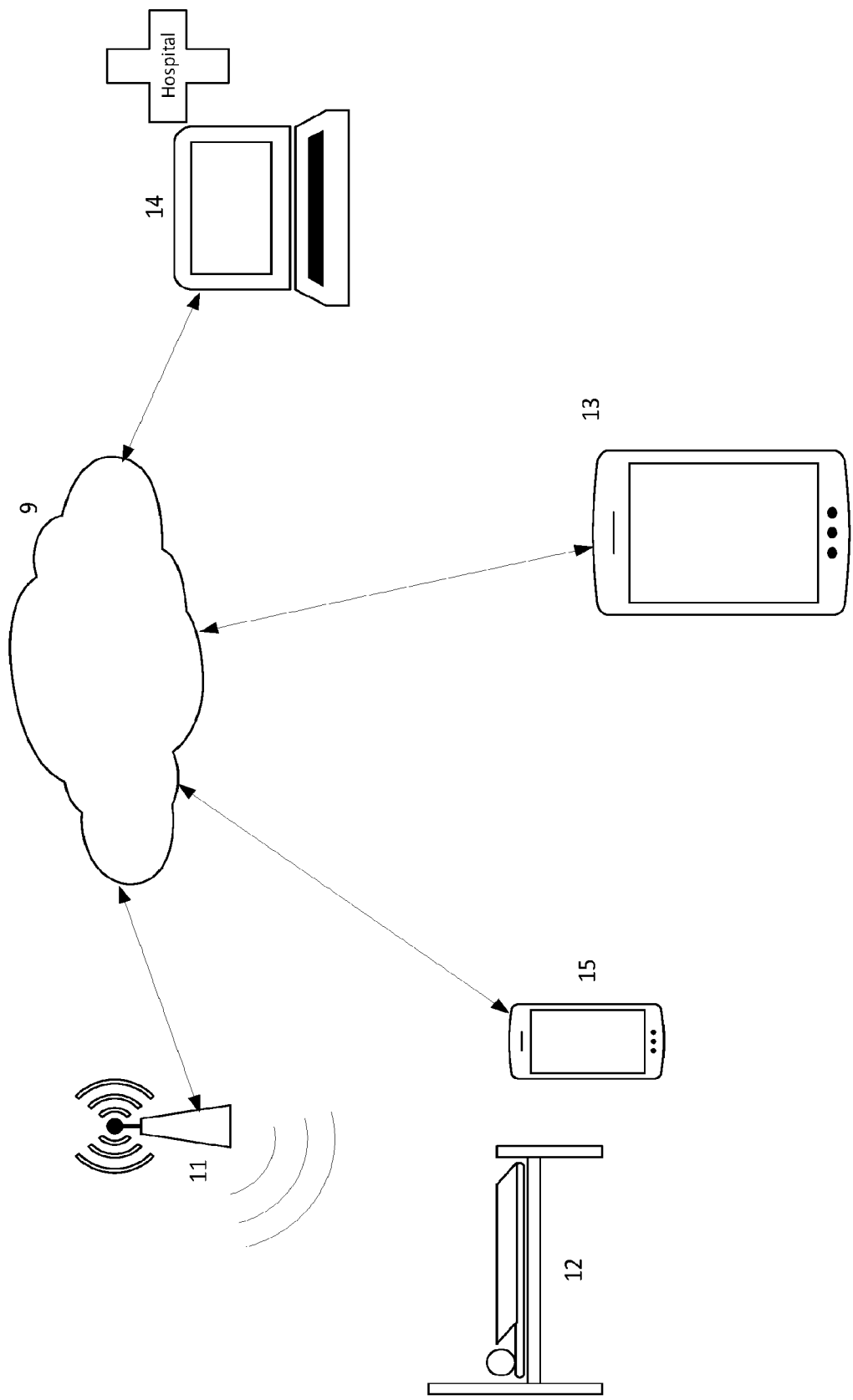
FIG. 1 is a functional diagram of an embodiment of a system according to the invention.

In the following description of various embodiments, reference will be made to the drawings, in which like reference numerals denote the same or corresponding elements. The drawings are not necessarily to scale. Instead, certain features may be shown exaggerated in scale or in a somewhat simplified or schematic manner, wherein certain conventional elements may have been left out in the interest of exemplifying the principles of the invention rather than cluttering the drawings with details that do not contribute to the understanding of these principles.

It should be noted that, unless otherwise stated, different features or elements may be combined with each other whether or not they have been described together as part of the same embodiment below. The combination of features or elements in the exemplary embodiments are done in order to facilitate understanding of the invention rather than limit its scope to a limited set of embodiments, and to the extent that alternative elements with substantially the same functionality are shown in respective embodiments, they are intended to be interchangeable, but for the sake of brevity, no attempt has been made to disclose a complete description of all possible permutations of features.

Furthermore, those with skill in the art will understand that the invention may be practiced without many of the details included in this detailed description. Conversely, some well-known structures or functions may not be shown or described in detail, in order to avoid unnecessarily obscuring the relevant description of the various implementations. The terminology used in the description presented below is intended to be interpreted in its broadest reasonable manner, even though it is being used in conjunction with a detailed description of certain specific implementations of the invention.

The present invention relates to devices, systems and methods for monitoring the health of patients and their activities in order to detect undesirable conditions or events as early as possible. The invention may be implemented in various embodiments, some of which will be described herein. In various embodiments a system according to the invention may be used as a sleep sensor (for sleep analysis), for monitoring of elderly, sick or other persons who require monitoring over time. A system will depend on sensors and in order to monitor a person in their sleep, physical placement may be in the ceiling over the person's bed, on a nightstand or bedside table, on the foot side of the bed, under the mattress, on the wall behind the bed (behind the head-part of the bed, above the head and angled towards the body), or on the side of the bed.

A device or system according to the invention may be configured to monitor e.g. posture in bed and movement in bed. Changes in patient medical condition over time may be captured, and can be used as a basis for patient monitoring, alerts/alarms, lifestyle change suggestions, medication effectiveness evaluation and more. In addition, more acute events, such as seizures or the patient falling out of bed, may be detected.

Two-way communication may be implemented in order to enable communication and alarms between a device and a caregiver, an alarm central, medical staff and/or relatives. Either by choice, such as activation by the patient, or automatically after an alarm/anomaly/notification.

In order to provide communication reliability, dual communication lines may be used for fallback if a single line fails. Among communication standards that may be used to provide the necessary communication capabilities are GSM/3G/4G/LTE and local broadband connection (WIFI).

In the embodiments below various conditions and events that may be monitored, detected or measured will be described. However, it is not practically possible to describe all possible combinations of what a system according to the invention may or may not monitor and detect. Rather, a system according to the invention may be configured to monitor any combination of the following and some of these will be discussed in further detail in the presentation of exemplary embodiments.

With respect to sleep, a system according to the invention may be configured to monitor one or more of sleep quality, hours in bed, sleep stage and hours in different sleep stages, time in bed before falling to sleep, total number of hours asleep.

A fall from the bed may be detected by measuring sudden displacement in the room.

Respiration may be monitored by measuring or detecting respiration rate (RPM), respiration variability, shortness of breath, stridor, abnormal respiration, sleep apnea, respiratory arrest, and respiration distress.

Heartrate may be monitored.

Detection of sound may be used to monitor or detect breathing sound, snoring, general respirations and sounds like stridor and wheezing, which may indicate trouble of breathing. Cries, scream, sound that indicate distress, cry of distress, and cry for help may be detected, and ambient noise (ambient sound) may be detected or suppressed.

In addition to monitoring or detecting the status of the patient, the system may also monitor the environment. Ambient sound has already been mentioned, and other variables that may be relevant to a patient's well-being and therefore monitored by a system according to the invention include air humidity, temperature, air pressure, brightness, color temperature of light in the room, air quality and VOC-sensor.

A system according to the invention may improve detection or prediction accuracy over time as it learns and understands the patient's "normal" behavior/activity etc.

The system may also be configured to detect movement in the room and register the number of people in the room.

In addition to the information directly provided through the sensors that are part of the system as such, a system according to the invention may also be configured to receive additional information from other sources. This may include logging in a mobile-app by the patient or by a caretaker, as well as measured or detected by third party equipment.

This additional information may include food habits, medicine (has the patient taken medicine or not), activity-/training measures, accelerometer, ECG, EMG, Melanoma/Skin device/app, hydration/dehydration, blood sugar, weight, body composition (bio impedance), blood pressure, oxygen saturation (SPO2-PPG), and electrodermal activity (sweat measurement).

A system according to the invention may be configured to provide alarms or notifications. Acute warning, or alarms, may be transmitted to relatives and/or health personnel or the like. Alarms may, for example, be activated upon detection of different kinds of seizure (e.g. epilepsy or other), respiratory insufficiency, fall out of bed, call for help, or sound that indicate distress. Less urgent notifications to relatives and/or health personnel may be issued when change occurs in the state of health of the measured patient (e.g. less sleep than normal, more seizures than usual, significant weight loss in short period of time, deviation in medication and more). This comprises a change from normal state.

In some embodiments an accelerometer is attached in/on the bed or attached to the patient.

According to one aspect of the invention, relatives or caregivers have access to a portal providing a simple overview of relevant health parameters and changes in these health parameters over time. This may include physical measurements such as weight, sleep quality and activity/training. Other information presented are the number of visits by home care personnel, notes from the home care personnel, planned activities and home care aids used (e.g. third-party devices).

A simple overview of relevant health parameters and change in these health parameters over time may include weight, sleep quality, physical activity/training, number of visits by the home care personnel, as well as notes from the home care personnel, planned activities such as doctor appointments, training sessions, and other future activities, general wellbeing and health status. The portal may further include information about or from additional aids and third-party devices used by the patient.

More detailed information may be provided through a medical portal. In this portal, medical personnel (for example a doctor) may have access to extended health information, health status of the patient, and other information that the patient or caregivers want to share. Medical personnel should quickly be able to get a clear overview of the patient's health status and seamlessly be able to immerse themselves in medical data with history over time, trends, statistics and comparisons of periodic data.

The medical portal meant for health personnel may differ depending on the patient diagnosis. For example, for a patient with respiratory problems, the treating physician may wish to see other data than what is relevant for one with epilepsy. The portal views may have different default configurations based on groups of diseases patients may suffer from.

Data displayed in the portal may include a combination of data selected from personal information, former and present health status, information about devices and assistance such as physical aids and personal help. Physical aids may include walkers, hearing aids, medical apparatuses, as well as other mechanical/electronical aids, while personal help may include home health care nurse, activator, physiotherapist, food deliveries, socializing aid, visitors and so on. The portal may further provide information related to number of visits by nurse/home health care provider, with comments/notes/pictures, female menstruation cycle, information regarding medication the patient is using, food habits (input form nurse/home health care provider or family/caregiver, picture sharing and picture bank/library for example for symptom logging, symptom log, a log of daily symptoms and a clear view of symptom history over time, patient/doctor diary, with possibility of sending simple messages, simple and detailed view of relevant health parameters and change of these over time, trends and so on, spikes and lows, and number of incidence of episodes.

The views of the portal can be adapted based on need, and information may be presented graphically, as numbers and with infographic. Comparison of health parameters may make it possible to see connections and gain a broader insight into the health of the patient. Warnings and notifications may indicate when parameters have been outside the normal range. The portal may provide detailed information about the parameters monitored by the system, such as sleep quality, heart rate, hear rate variability, blood pressure, oxygen saturation, activity/work-out, weight, seizure, and critical/not critical episodes.

One embodiment of the invention also includes detection of epileptic seizure. In this embodiment the system may analyzes movement and may further include a combination of sound, respiration and heart rate data to evaluate or detect a seizure. The system may include view and analysis over time in order to observe trends over time and use smart algorithms and machine learning to recognize seizure triggers (For example caffeine, activity level (lack of and/or too much), medication, medication adherence and much more.

Embodiments of the invention may include various sensors and peripheral devices, including measuring sensors for many different parameters, such as UWB, audio (microphone), air humidity, temperature, brightness, light color temperature, and air quality.

Feedback to user communication interfaces, including configuration and debugging, may include speaker, Bluetooth, BLE (Bluetooth Low Energy), Zigbee, Z-Wave, GSM/3G/4G, Apple Homekit, Apple Healthkit, Apple researchkit, WiFi, Status-LED/lighting/screen for feedback to user, and infrared.

Further components may include micro controller, power supply, USB interface, medical grade casing, battery for battery operation, battery management technology, wireless battery charging, and integration with 3rd party building/home automation equipment such as lighting, temperature control and more.

The system may also include an app for logging of relevant data (such as medical intake, symptoms, physical activity (either entered or measured from mobile device) and more, communication between patient and medical staff and patient and caregiver/relatives. In addition, for presenting relevant data to the patient and to the caregiver/relatives.

Such an app could provide a method of sharing pictures and picture bank/library, for symptom log, as well as logging of data such as medical intake, symptoms, physical activity (either entered or measured from mobile device), female menstruation cycle, activity data, social life data, mood, stress level (felt stress and measured cortisol level), and blood test data.

In some embodiments the system may also provide or enable communication between medical staff and patient and caregiver/relatives. In addition, the system may also be configured to present relevant data to the patient and to the caregiver/relatives in order to give them insight to their health data in a clear and understanding way.

Notifications may be provided by the system, such as feedback when successfully logged data over time, when reaching goals and more, health changes (positive and negative), advice on when to seek out health personnel, and health notifications when anomalies occur or data are outside the normal range. physical design of the device/unite.

The local device may include an attachment plate for fixed installation on wall or ceiling (with quick release function). An adjustable stand may provide the user with the freedom to place the device on a nightstand.

The device may be completely wireless when running on battery power.

As described above, the device may have multiple different sensors, which will be described now. It should be noted that various embodiments of the invention may include only a subset of the sensors described herein. Also, additional sensors not included in this disclosure may be included in various embodiments.

UWB (radar) may be configured for motion detection, multiple environmental sensors (temperature, pressure, light and more) may be used to detect additional parameters. Respiration can be detected by recognizing chest movement.

Sleep analysis can be performed with the device registering sleep and sleep pattern by analyzing respiration, movement in bed, and in some embodiments also sound/audio. Measurements may then be analyzed, and both acute changes that may be indicative of emergency situations, as well as less serious events, are captured. Changes over time, which would not otherwise be easily detected when viewing short-term data, can thus be detected. Machine learning may be applied for pattern recognition and anomaly detection.

3rd party equipment can be connected to the system for a more thorough analysis of the patients situation/state. For instance, medical dispensers can be connected and combined with other data to see how changes in medical dosage/medicine/forgotten dosage affects the patients symptoms, general health and wellbeing and sleep quality. Another example is the addition of activity trackers to monitor how physical activity affects sleep quality, health and symptoms and the other way around.

A machine-learning algorithm may be applied to analyze data from the device—either as a stand-alone sensor or in combination with third party equipment to better recognize the patient's situation, and to provide recommendations, indicate relations between symptoms/health and other factors and/or to provide insight into the measured data.

Audio recorded by the sensor can be analyzed using machine learning algorithms to recognize sounds such as normal breath, respiration distress, distress, stridor, apnea, sleep talking, speech, snoring and more. Acute situations/conditions automatically trigger alarms, while non-acute situations/conditions are logged and analyzed with machine learning algorithms (either locally in the device or off-site/in a cloud based back-end system). Any data recorded can be presented to the patient, caregiver, relative, health personnel etc. either in unprocessed format, with signal processing applied or after applying machine learning.

The patient's condition and associated recorded data is tracked over time and continuously evaluated by machine learning algorithms. Algorithms track changes over time and learns from the patient data to increase precision over time.

Different machine learning algorithms may be applied, such as (but not limited to) timeseries analysis, anomaly detection, classification, regression and deep learning algorithms. Big data analysis, dimensionality reduction and clustering algorithms may also be applied, mostly in the back-end part of the system. Machine learning algorithms may be applied locally in the device (edge computing), in the back-end system or a combination of both.

Data from the sensor can be transferred in either of the two communication lines. Sensor status messages may also be transmitted, and any sensor error, communication problem etc. is transferred when at least one communication line is working. This information may be transmitted to the system provider or health care provider or other relevant personnel.

The invention provides solutions that may be configured to or address the needs of different types of patients or users. Among such users are the elderly, people who are Ill and chronically ill, as baby monitor, and athletes, but also for regular consumers who do not have any specific needs, but who would like to monitor aspects of their health.

As such, the present invention includes embodiments addressing or adaptable to the needs of the consumer market, health care institutions, hospitals, special hospital and home health care service.

Having thus presented an overview of parts of the system according to the invention and its functionality, a more detailed description will be given in the form of exemplary embodiments, aspects of which are illustrated in the attached drawings.

FIG. 1 is an overview of an exemplary system according to the invention. The drawing shows a patient in bed 12 being monitored by a sensor 11, which may be a UWB sensor which may be capable of detecting movement including respiration and falls. The sensor 11 is in communication with back end services in the cloud 9. It should be noted that in this drawing local equipment is illustrated as a single sensor device. As will be described in further detail below, the local device may be in communication with several sensors in a room.

The communication between the local device/sensor 11 and the back end cloud service 9 may include redundancy, i.e. it may include several communication links of different types, as described above.

The patient may have a cellphone or smartphone 15 which is also in communication with the cloud service 9. The smartphone 15 may be used by the patient to input data, for example about meals, medication and activities, to access data available from the could service 9, or sensors in the smartphone 15 may provide supplementary information, for example about location (GPS), steps walked by the patient, etc.

Also illustrated is a tablet device 13 representing the access relatives of the patient may have to data from the cloud service 9, and a laptop computer 14 representing access by medical personnel for retrieving or entering information.

Figure 2:
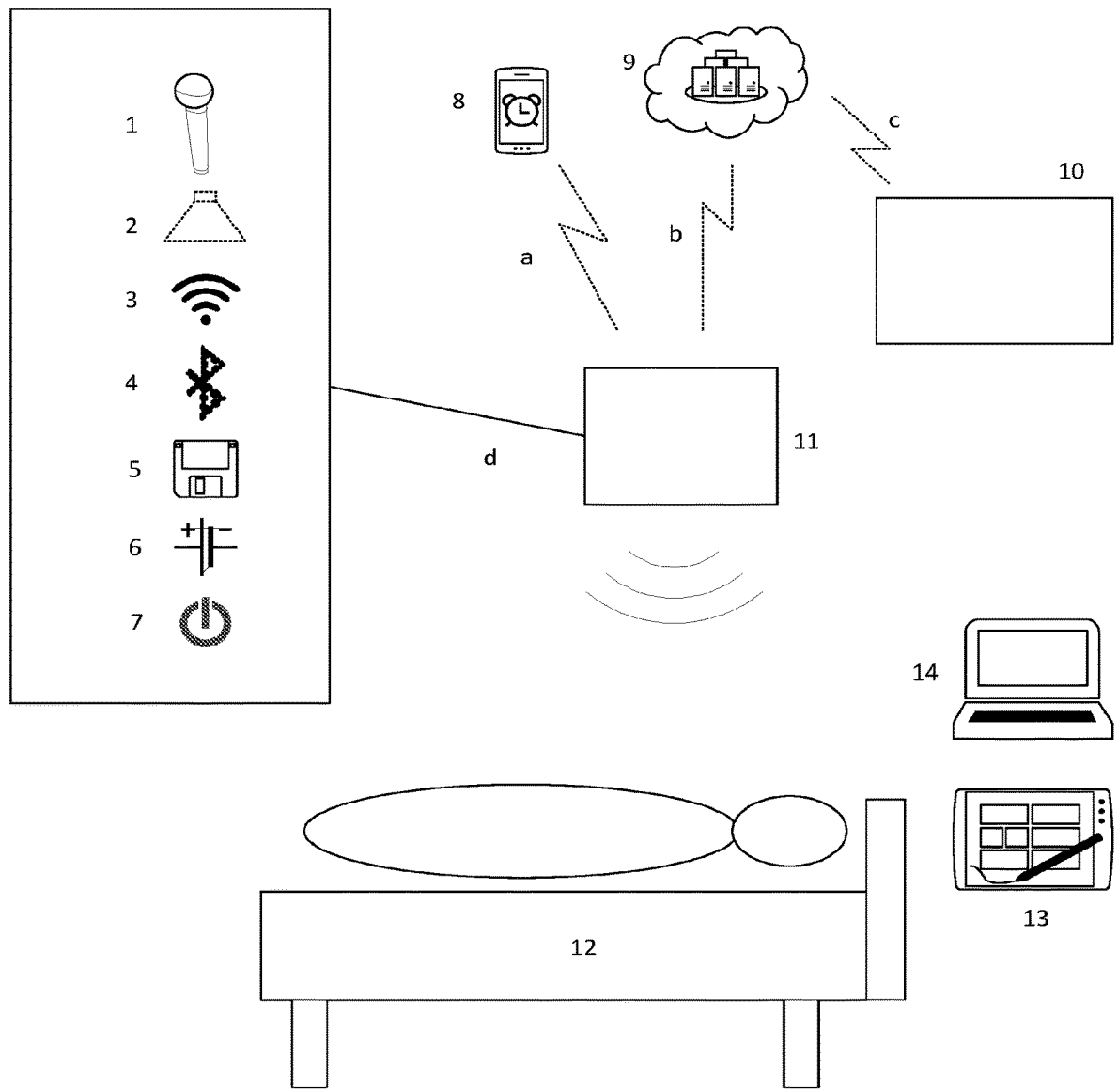
FIG. 2 is a detailed view of a local device and connected equipment.

Reference is now made to FIG. 2 which shows the local device 11 in further detail.

The sensor or local device 11 includes or is connected to a microphone 1 with dual purpose. Firstly, the microphone 1 may serve as a communication path from the patient to the recipient, allowing the recipient to listen to any voice or audible noises from the room where the sensor is placed. Also serves to allow voice communication between patient and recipient, either as one-way communication, or as two-way communication when in conjunction with Speaker (2).

Secondly, the microphone 11 provides audio input to audio distress monitoring system. Algorithms, signal processing and machine learning may then be applied to identify audible signs of distress, which may trigger an alarm.

A speaker 2 is configured to deliver audio-feedback from the sensor device 11, and functions as a speaker for voice communications when used to communicate with recipient.

Wifi capabilities 3 may be used for communication between the device 11 and either other local devices for storage and/or processing, and/or to connect to a local access point to communicate with the back-end server 9. WiFi may also be used for device configuration or update.

Bluetooth or Bluetooth Low Energy (BLE) 4 may also be a communication capability implemented in the local device 11, and it may be used for communication between the device 11 and local tablet or phone for configuration purposes. Bluetooth 4 may also be used to communicate with other local devices.

Local storage 5 may be used for non-volatile data storage of sensor data, including raw data, timestamps, events, sensor status and more. This storage can act as a buffer before uploading to back-end server, depending on communication pathway availability.

A battery 6 may be used for battery powered use, or as backup power during power outage when the device 11 is connected to a power outlet.

The device 11 may also include a user interface for user input of commands or instructions, such as physical buttons or a touch screen. User input may include on/off.

A mobile phone 8, or cellular, communication capability may also be part of the device 11. This communication capability may implement one or more cellular standards, including GSM, 2G, 2.5G, 3G, 4G, 5G and any mobile future technology. The device may also include landline (PSTN), IP or other phone technology. This communication capability may be used for receiving alarms, alerts, and vocal communication. An app may be used to allow for sensor-device status monitoring and history. For redundancy, communication can be established through a secondary communication channel. A list of multiple recipients may be used, including national emergency numbers. Secondary communication channels can include any form of communication line, including Wi-Fi or secondary mobile network.

In the drawing, this communication capability is represented as a smartphone. This should not be interpreted as a limitation on the invention. This communication capability may typically be implemented as one or more modules in the local device 11. However, it is also consistent with the principles of the invention to use an external device to implement this communication capability, and this external device may be connected to the local device 11 by cable or wirelessly, for example using the Bluetooth capability 4. In some embodiments using an external communication device 8, the patient's smartphone 15 may be used to provide this capability.

The cloud storage and data processing 9 backend system may implement machine learning algorithms that are used to analyze data. Data from other sources (3rd party equipment) can be integrated into the platform here. The cloud based service may deliver personalized recommendations and interpretations based on data from either the sensors connected to the local device 11, 3rd party sensors, other sources of information, e.g. manually logged data, or a combination of two or more such sources. These recommendations or interpretations may be provided to the patient themselves, caregiver(s) (doctor, hospital etc), and relatives.

Wireless communication for data communication (e.g. Wi-Fi) may fall back to mobile communication when necessary. Mobile communication may be used for status messages, through SMS or data transmissions.

As mentioned above, the system may allow connection of third party equipment. Data from such third party equipment may be imported by the cloud service 9 and integrated into the data provided by the sensors and devices connected to the service.

The local device 11 may, as mentioned above, include one or more sensors, be connected to one or more sensors, or both. In the present disclosure the sensors will be described as extensions or capabilities of the local device 11, and for the purposes of data origin and flow reference to the sensors and reference to the local device 11 are not intended to be interpreted as categorically different.

The patient 12 being monitored may be immobile (lying in bed, on the floor, sitting in a chair or other) or mobile (moving, walking).

Tablet 13, mobile phone 15 or computer 14 may be used for presentation of data from the sensors and the platform. As mentioned above, presented information may include sleep events, sleep quality, dietary information, medical information, drugs and more.

As described with reference to FIG. 1, these devices do not have to be locally present, and may belong to caregivers, relatives, health personnel or others with access to the cloud service 9. In particular, healthcare provider or non-professional caregiver HMI. A computer 14 shows data which the patient chooses to share.

Figure 3:
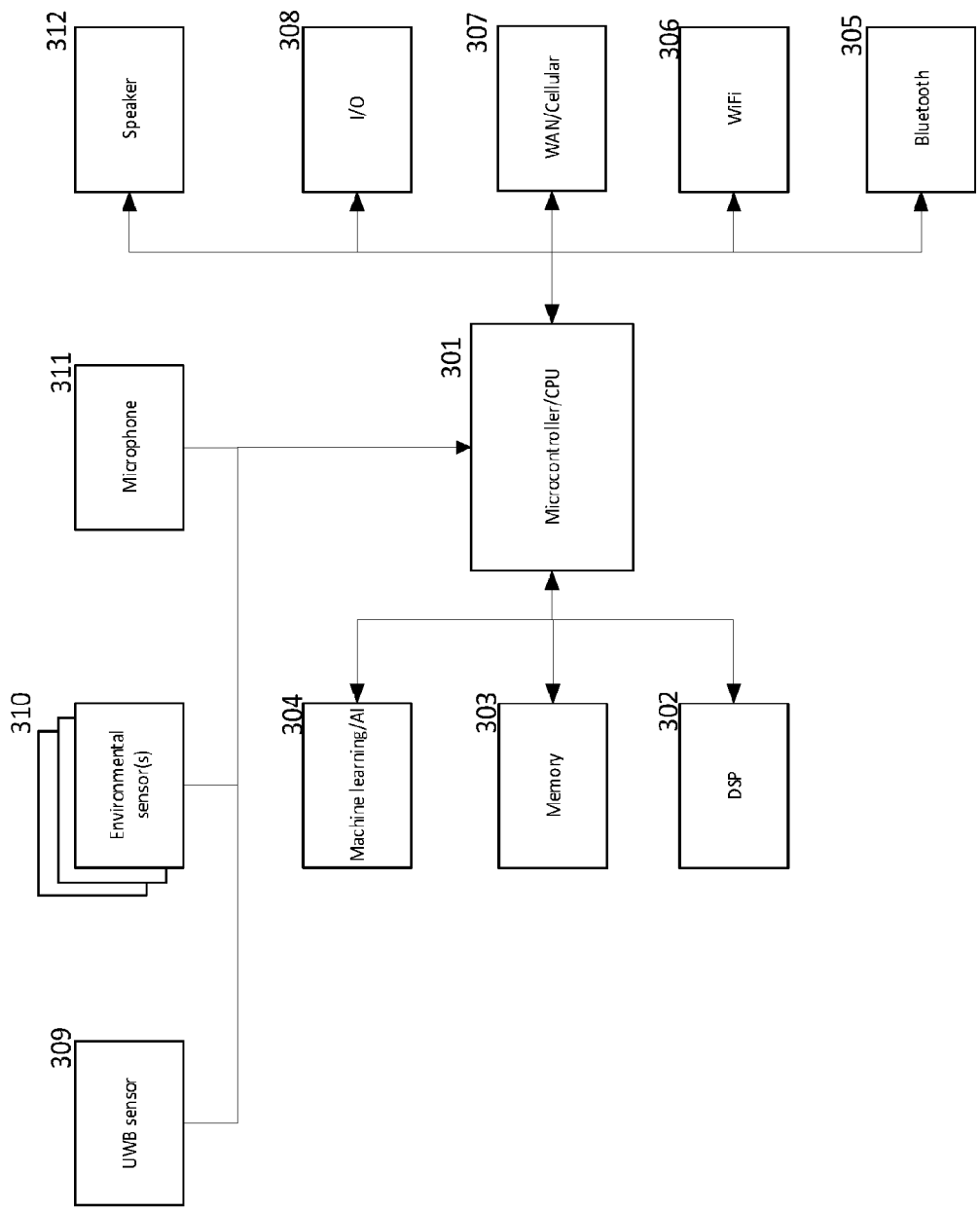
FIG. 3 is a block diagram showing modules of a local device according to an embodiment of the invention.

FIG. 3 is a block diagram of an embodiment of a local device 11 consistent with the principles of the invention. The various blocks represent hardware modules, but at least some of them will depend on software modules that are embedded in the modules itself or stored in device memory. It should be realized that functionality may be distributed between several hardware modules or combined in the same hardware module. Also, some functionality may be implemented in the cloud service 9 back end rather than on the local device.

The device 11 includes a microcontroller, system on a chip (SoC) or single board computer 301, which may include one or more CPUs or processor cores. The microcontroller 301 may further include or be connected a digital signal processor (DSP) 302, memory 303 and a machine learning module 304. These modules may be embedded in the microcontroller 301 or they may be separate modules. The machine-learning module 304 may implement one or more machine learning and artificial intelligence algorithms. In some embodiments the signal processing and/or machine learning requirements are such that one or both of these modules are unnecessary and signal processing and/or adaptation may be handled by the microcontroller/CPU 301 based on software stored in memory 303. In other embodiments, some signal processing or machine learning is performed in the cloud 9.

The microcontroller 301 is also connected to communications modules. In this embodiment a first communication module is a Bluetooth module 305 capable of establishing wireless communication with other devices in the vicinity of the local device 11. Bluetooth Low Energy (BLE) may be used between device and mobile phone/computer for first-time configuration of the device 11, or later reconfiguration.

A Wi-Fi module 306 may also be provided. Wi-Fi may be used for local communication between device and HUB or gateway, or between devices if configured in a MESH-network.

A Wide Area Network (WAN) or cellular network module 307 may be provided and serve to provide an alternative wireless communication capability (i.e. fallback communication) which may be used if a Wi-Fi connection cannot be obtained or if the Wi-Fi connection loses connectivity with the cloud service 9. This module 307 may implement one or more of GSM, LTE, 4G, 5G or other such technology.

A basic input/output module 308 may provide wired communication. This will typically be Ethernet, but other standards and technologies can be used. Power over Ethernet (PoE) may be used to power the device from the same interface/cable. This communication interface serves the same purpose as the wireless module for local communication, and is the primary communication channel when available. In such case, the wireless is the redundancy communication channel, and serves as a backup.

An ultra-wideband (UWB) sensor 309 is configured to monitor the environment occupied by the patient and provide input data to the local device 11. In some embodiments the UWB sensor is part of the local device 11 and may even be mounted on the same printed circuit board as the microcontroller 301. It is, however, in accordance with the invention to provide an UWB sensor 309 external to the local device 11. For example, the local device 11 may be place on a nightstand or bedside table while the UWB sensor 309 may be mounted on a wall or ceiling. If the UWB sensor 309 is external to the device 11 the two may communicate using, for example, the Bluetooth module 305 or the I/O module 308.

Different UWB sensors are commercially available, and may be used in conjunction with the invention. Examples include Xethru X4 and Xethru X2 from Novelda AS, a Norwegian company, as well as alternatives available from Vayyar Imaging Ltd, an Israeli company. (Xethru, and Vayyar are registered trademarks.) Some such sensors, for example those provided by Vayyar, detect direction from the position of the sensor, i.e. a position in a sensor plane, as well as distance from sensor to object. This makes it possible to generate a 3D representation of presence and motion. Some embodiments of the invention use machine learning on such 3D input in order to develop more sophisticated pattern recognition models and enabling detection of additional conditions or detection with higher accuracy.

In some embodiments, the UWB sensor 309 is supplemented by one or more environmental sensors 310. These may include a thermometer for sensing temperatures in the room where device is installed, a photodetector for detecting brightness and color temperature of the lighting in the room, an air quality sensor detecting volatile organic compounds (VOC) and/or carbon dioxide reading ($CO_2$). Other sensors may also be connected, permanently or intermittently, including a barometer for measuring air pressure, a heart rate sensor connected to the patient for measuring heart rate or heart rate variability, sleep sensor mats, blood pressure sensor, etc.

A microphone 311 may be provided for detection of vocal distress (calls for help, screams, crying etc.), snoring, signs of epileptic seizures and more. Audio signals may be processed by the DSP in order to detect, classify or measure sounds.

The local storage 303, which may be embedded in the microcontroller 301, external to the microcontroller, or a combination of both, may be used to store instructions including the operating system, the machine learning algorithm(s), other signal processing algorithms and other software instructions to be executed by the processor cores, the DSP 302, the Machine learning/AI module 304, and also for caching of data, storage of readings in case of communication dropout and more.

The speaker 312 may be used to play audible alarms, to provide communication with remote devices, play audible system sounds, etc. The speaker 312 may be internal to the device 11 or an external speaker may be connected to the device 11 using an appropriate connector. The device 11 will include the necessary audio drivers, digital to analog and analog to digital converters, etc. These are not illustrated, but they may be implemented as part of the microcontroller 301 or as separate modules, or a combination.

The UWB sensor 309, whether it is embedded in the local device 11 or is external to the device and in wireless or wired communication with it, must be positioned such that it has an appropriate view of the area, usually a room, where the patient is located. Possible locations include in the ceiling above the patient's bed, on the wall at the head or foot of the bed, on a bedside table or nightstand, in or under the mattress or under the bed. The UWB signal is able to penetrate most furniture, so direct line of sight is not a requirement. Other locations are therefore also possible.

The UWB sensor 309 is capable of detecting events, or strictly speaking, providing a radar signal that carries information indicative of events such as movement, presence, absence, epileptic seizures, respiration, heart rate and falls of a patient in and around the bed. The UWB sensor measures these events by sending out electromagnetic waves in the GHz range and processes the reflected return signal to calculate the distance to the reflecting object.

Different UWB sensors that may be used in conjunction with the invention are commercially available. In some embodiments the UWB sensor includes two or more transmitting and receiving antennas and electronics for electromagnetic pulse generation, signal processing etc. The working principle of the UWB sensor is that it detects minute changes in an object's movement by phase and frequency modulation of the reflected electromagnetic wave as well as time difference of transmitted and received electromagnetic wave. This enables detection of presence, absence, distance, movement, respiration (i.e. movement of thorax) and heart rate (Small movement/vibrations in thorax). Specifics may vary with respect to both the characteristics and duration of the transmitted signal and the signal processing of the received signal (the radar echo). These are well known in the art and not part of the invention as such. Different strategies may be selected for the radar pulses both with respect to the shape of the signal (narrow base band pulses, frequency sweeps, frequency jumps) and with respect to how often pulses are emitted (sampling rate). It is believed that anywhere between 10 and 100 samples per second may be adequate, but this is a design parameter that may be adjusted based on circumstances and other features of the system as a whole.

The principle of using UWB sensor measurement of a patient's vital signs, primarily heart rate and respiration, are known in the art. According to these methods UWB is used to measure movement of the patient's chest and heart caused by inhaling and exhaling and by heartbeats. These movements are small and relatively regular and they can easily be isolated from noise and random body movement and subsequently analyzed using the Fast Fourier transform (FFT).

These methods are known in the art and will not be described in further detail herein. Reference is made to "A Detailed Algorithm for Vital Sign Monitoring of a Stationary/Non-Stationary Human through IR-UWB Radar" by Faheem Khan and Sung Ho Cho, available online from PMC, US National Library of Medicine, National Institute of Health, at https://www.ncbi.nlm.nih.gov/pmc/articles/PMC5336124/ and hereby incorporated by reference in its entirety.

Figure 4:
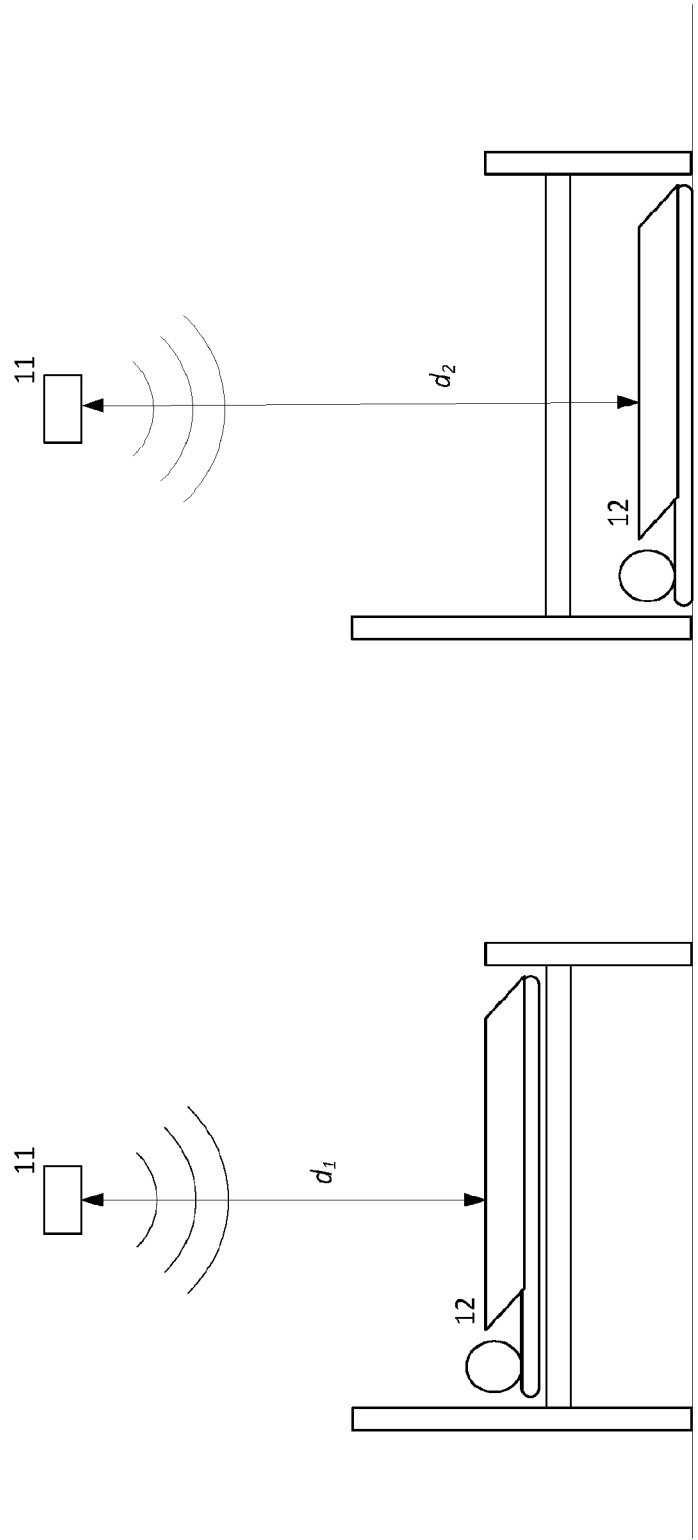
FIG. 4 illustrates how a sensor detects different distances to a patient in bed and a patient who has fallen out of bed.

Reference is now made to FIG. 4, which illustrates the principles of fall detection according to one embodiment of the invention. Detection of respiration and heartrate, as referenced above, is based on detection of regular movements and use of auto-correlation techniques and observation of harmonics, while random body movement is undesirable and its effects must be eliminated, for example by discarding vital signs measurements during periods of random body movement. As opposed to this, the present invention is capable of specifically monitoring random body movement and attempt to detect and classify such movement in order to detect or predict events that require the attention of health personnel or other caregivers.

The example illustrated in FIG. 4 is that of a person 12 having fallen out of bed. In this example the local device 11, or at least the UWB sensor that is part of or connected to the local device, is mounted above the bed and measures the distance down to the patient's chest $d_1$. After the patient 12 falls out of the bed the distance increases to $d_2$. The local device may have been configured to include a trained model (also known as a pre-trained model), that has been generated through machine learning performed on aggregated data obtained through observation of other patients in similar situations. This model provides the ability to identify a fall, not simply based on the distances $d_1$ and $d_2$, but on the progression of the measured distance from the starting position in the bed to the final position on the floor, which can be recognized as a pattern in accordance with the training of the model.

Figure 5:
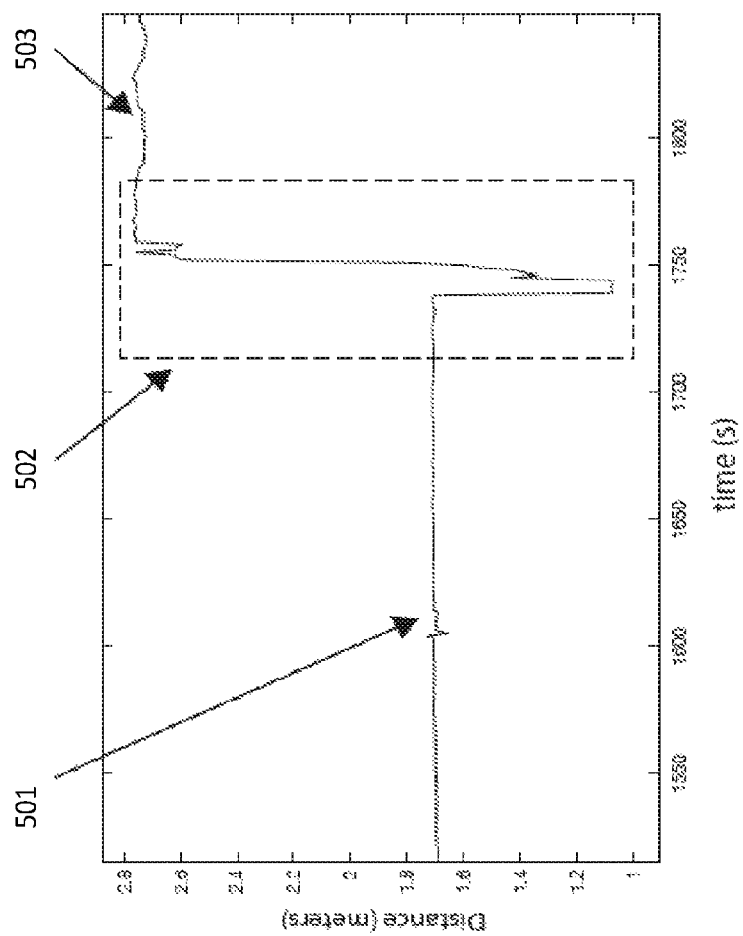
FIG. 5 is a curve illustrating an example of the distance from a sensor to a patient during a fall.

FIG. 5 shows the measurement generated by the local device 11 when a patient falls out of bed. The curve represents the distance from the sensor to the patient, and initially the distance is as shown by the curve during a first period of time 501. Then, when the person falls out of bed the signal goes through a period of transition 502. First, the distance to the person is reduced, probably because the patient is getting up. The distance then suddenly increases from approximately 1 meter to approximately 2.7 meter when the person falls. After this transition a new stable period 503 starts; apparently the patient cannot get back up.

It should be noted that while this example seems straightforward, with not much chance of drawing the wrong conclusion, many situations are not so clear-cut. For example, some actual falls may be difficult to detect, for example if the person loses their balance, falls partly back on the bed and slides down on the floor, the transition takes more time and can perhaps not be detected simply because of the sharp transition. Other examples include situations that are not falls, but that do include a relatively sharp transition, for example if the person sits or lies down rapidly. The patient may even lie down on the floor, for example in order to perform exercises.

The layout of the room itself may create additional difficulties.

Consequently, machine learning algorithms which are able to adapt and learn how to disregard behavior that is not associated with an undesirable event, as well as improve detection and classification of real events may be used to obtain better results than that which is possible using a model based on theory and assumptions. This means that a device or system operating in accordance with the principles of the invention will continuously improve its ability to make correct interpretations and predictions of events, and this improvement not only continue over time, but will also adapt to any changes in the health condition of the patient.

This ability to adapt is not limited to detection of falls, as detection of falls is only one possible use where the present invention may be of utility. Other use cases include health monitoring of patients in nursing homes, care facilities or similar. Each patient room may have a local device 11 installed therein and optionally additional sensors and devices may be provided. Healthcare staff may have access to patient related information generated or collected by the system, dependent on access level. The system is capable of providing full overview and detailed information about each patient, as will be described in further detail below.

The system may also be used for remote health monitoring of patients in residential homes, clusters of elderly assisted living or similar.

Health monitoring of elderly or patients with health related conditions may be done at home with optional remote warnings/alerts to alarm centrals, family, relatives or similar. Sensors may then be installed in several rooms, particularly rooms that are extensively occupied or associated with increased risk for home accidents; bedrooms, living rooms, kitchen and bathrooms may be prioritized.

A local device 11, or the cloud based service in embodiments where sensor data is transmitted from the local device 11 to the cloud service 9 for processing there, can be configured to process data based on a particular model. The model may include methods for feature detection and classification such that known features are detected in the sensor input and classified as representative of known events or conditions. The definition of such models may be based on a number of feature extraction algorithms that are known in the art. In some embodiments, the model is a pre-trained model that has been built using machine learning on data collected through monitoring of patients and classification of events. A model may be specifically trained to detect specific events, some of which will now be described.

Presence detection may determine whether a patient actually is present in a room. Embodiments implementing presence detection may further monitor if the patient is in bed, how long the patient has been in or out of bed, and transmit an alert message if the patient has been in or out of bed for a defined period of time. The (in or) out-of-bed alert timeframe may be adjustable and depend on individual need and requirements. Furthermore, the alert timeframe may be automatically adjusted by the machine learning algorithm. For example, the system may learn that a monitored patient usually gets out of bed for five minutes each night, and determines that an absence for 20 minutes one night is an anomaly that may trigger an alarm.

Fall detection has already been described and is configured to detect falls by analyzing the distance from UWB sensor to resident. The system may, for instance, detect if it is a slow or a fast fall by analyzing the distance, time difference in changed distance and velocity of the patient falling. Furthermore, the system may be able to detect the health state of the patient after the fall by analyzing if the patient is moving or not, and if breathing while laying on the floor, for instance.

Epileptic- and non-epileptic seizures may be detected by analyzing movement pattern as well as the vital signs of the patient pre-, during- and post-seizures. The system may be configured to alert caregivers if a seizure is detected, enabling healthcare staff and caregivers to promptly give appropriate care to the patient. Prompt care for patients experiencing a seizure will remedy any possible and unnecessary damage suffered by the patient and help reduce the number of occurrences of SUDEP (Sudden Unexpected Death in Epilepsy). The reasons causing SUDEP are not fully known, but it is believed that that rapid response when patients experience seizures at night is of vital importance.

Audio analysis may be supplemental to the processing of UWB radar data. Embodiments of the invention enables analysis of audio in the local device 11 or in the cloud 9, to detect sounds of distress. Examples of such distress can be muffled or high-pitch calls for help, crying, snoring, distinct sounds made by the patient during a seizure, or other sounds that may be related to distress. Applying machine learning to the combination of UWB radar input and audio input may help the system develop an improved model for detection or prediction of seizures adapted to specific patients.

Many old and invalid patients have issues with pressure ulcers caused by lying in bed over longer periods of time and not being able to turn their body unassisted. Such patients need help from healthcare staff to turn around in bed at appropriate intervals in order to avoid pressure ulcers. With an appropriately trained model, the system may analyze the movements of patients that are in danger of pressure ulcers and alert healthcare staff that the patient needs to be turned.

Appropriately trained models may be used to analyze the patient's quality of sleep by analyzing the movement and breathing pattern during sleep. This enables quantification of different sleep stages and if the patient has slept uneasy or not.

The invention may also be configured to detect respiration distress such as, but not limited to, difficulty of breathing, sleep apnea or hypo-/hyper ventilation by analyzing the breathing pattern of the monitored individual. Similarly, the invention may be configured to detect arrhythmia from resting heart rate when a patient is sleeping in bed during daytime or nighttime.

Health deterioration detection can be based on long term monitoring of the patient. The invention may, in embodiments implementing this capability, give feedback to healthcare staff or caregivers if a patient has deteriorating health. Health deterioration may be detected by analyzing the data gathered by the UWB sensor, other sensors/devices and other health data such as known sickness, medicine/drug usage/dosage or other relevant information from a patient journal. The system provides a historical overview of the patient's health which makes it easy to see if there is a downward trend in health condition and thus enable healthcare staff and caregivers to start countermeasures to avoid unnecessary suffering and hospitalizations.

The invention enables the construction of personalized models using advanced machine learning that learns the health patterns of the patient and is thus able to more accurately detect lowered health state than using one-fits-all algorithms. The models enable detection of patterns in the sensor data input that enable prediction or detection of events.

Furthermore, combination of random body movement (RBM), vital signs monitoring, other types of sensors and devices and combined analysis of data from two or more sensors and devices enable the system to gain deeper insight into the patient health and to train models for detection or prediction of a wide range of conditions and events.

The ability to install or create recognition and prediction models for a wide range of conditions and events provides a system that is highly adaptable and may be customized to meet the needs of individual patients. Adaptation can be done to meet the specific needs of a patient. If the patient is predisposed or has a history of falls the system can be adjusted to prevent falls in addition to detect falls. For instance, based on machine learning the system can adapt such that it will issue an alert or a warning if a patient is about get out of bed or adjust the timeframe for how long patient is out of bed based on past events associated with getting out of bed or normal absence from bed during the night. Furthermore, the invention allows for connection of any additional sensors or devices to meet any patient needs. A system according to the invention may in some embodiments be configured to connect to and receive data from any system specific or 3rd party sensor or device to cover any specific needs of a specific patient towards enhanced health monitoring. Applicable sensors or devices include, but are not limited to, ECG (electrocardiograph), EMG (electromyograph), EEG (electroencephalograph), spO2 sensor, temperature sensor, HRM (heart rate monitor), VOC (volatile organic compound) sensor, $CO_2$ sensor, or other wearable or non-wearable monitoring devices.

The cloud service 9 may in some embodiments of the invention be configured to enable distribution of health related information to the patients themselves, to health care personnel and caregivers, and to relatives. The continuous monitoring of a patient's current situation as well as continuous health status can be made accessible and visible through numerous user interfaces on phones, tablets, computers and other electronic devices, for example based on well known web technology (such as HTTP, HTML, XML, CSS, Javascript, etc.) and delivered through data communication networks, typically wide area networks using internet protocols (TCP/IP), as well as cellular networks and other available communication channels. The health status of the patients may be made accessible in different layers, which gives access to different amount of detailed information dependent on access rights.

This may be utilized to provide health care staff, caregivers, family members, guardians or similar with alarms, alerts or warnings if, for example, the monitored patient's health has deteriorated, if a person has been out of bed for longer than a defined number of minutes, or if a critical event such as a fall or a seizure is predicted or detected. The alarms, alerts or warnings may be provided in different severity levels enabling the caregiver to prioritize if there are other alarms, alerts or warnings present in the system. The alarms, alerts or warnings may be presented in a GUI installed on a phone, tablet, computer or a similar device, either in a dedicated app, or by using a standard web browser. In some embodiments the system may require that alarms, alerts or warnings are acknowledged by a user verifying that the person in need is attended to. After the person has been attended to the caregiver resets the alarms, alerts or warnings and the system reverts to normal state without alarms, alerts or warnings. In some embodiments, the definitions of alarms, alerts and warnings are as follows: Alarms are issued when there is a sudden change in health state such as a detection of a fall or an epileptic seizure. Alerts are issued when there is a known state of deteriorating health where a patient needs increased surveillance over longer periods of time, for instance if a patient has got the flu or after a fall has occurred. Warnings are issued when the system detects events in which there are some uncertainty of the patient health state, such as being out of bed for a defined number of minutes or it has been to long since it has been registered that the patient has taken or received appropriate medicine. Other ways of classifying and prioritizing messages generated by the system are, of course, possible within the scope of the invention.

Figure 6:
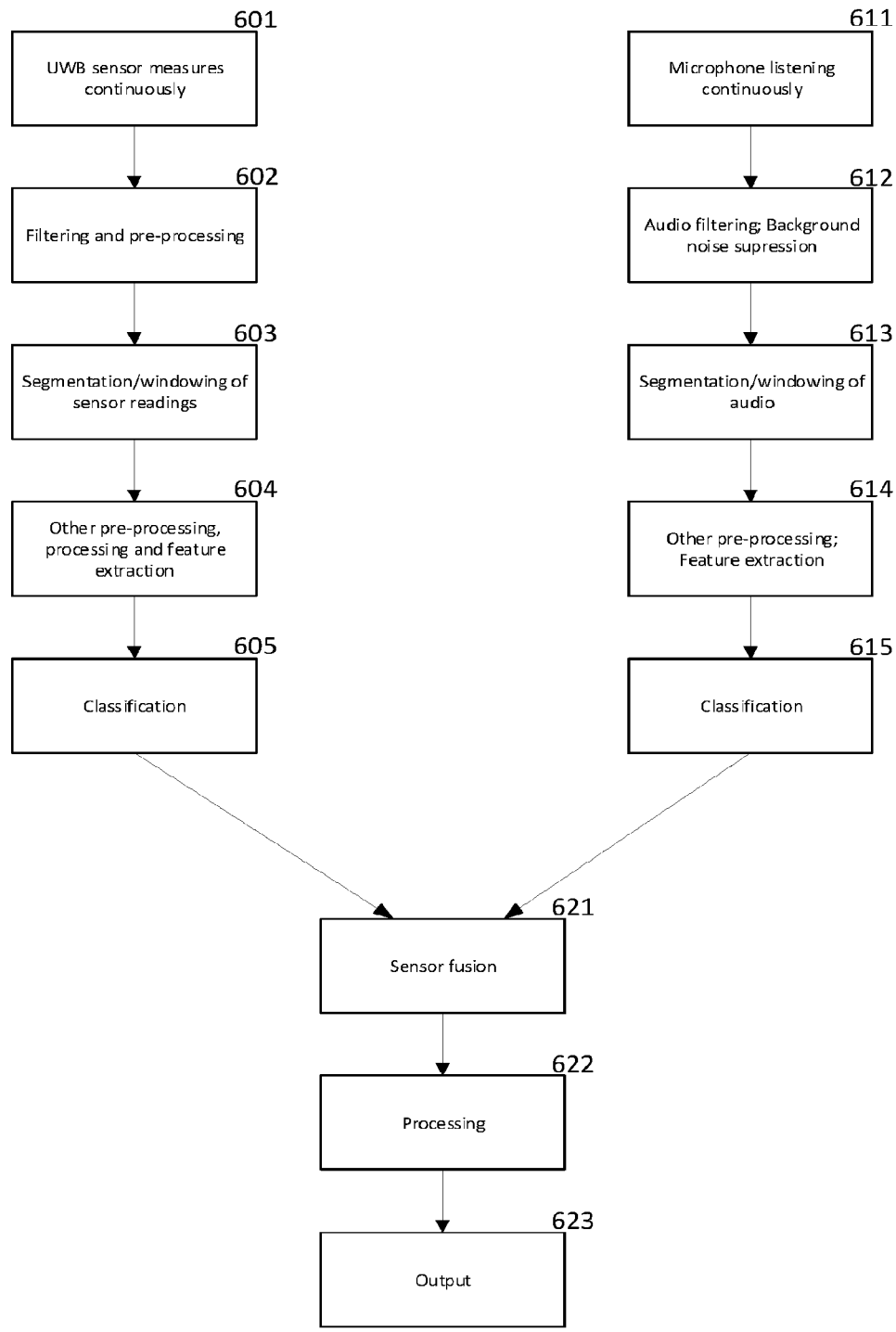
FIG. 6 is a flow chart illustrating pattern recognition performed on sensor data from two sensors in accordance with an embodiment of the invention.

FIG. 6 shows an example of how sensor data from several sensors can be processed and utilized in embodiments of the invention. A first sensor, which may be a UWB radar, monitors an area continuously 601. The reflected radar signal received by the UWB radar is filtered and pre-processed in step 602. The exact nature of this filtering and pre-processing may vary depending on the shape or characteristics of the radar signal transmitted by the UWB radar, as well as the requirements of the subsequent processing of the signal. Among the techniques that may be used during pre-processing are band-pass filtering, fast Fourier transformation, wavelet transformation, Kalman filtering, decorrelation, and more. The most important purpose of this pre-processing is to prepare the signal for classification by removing unwanted artifacts, and reducing noise and autocorrelation.

In a next step 603, the filtered and pre-processed signals may be segmented in order prepare the data for further processing in well-defined data frames, something that i.a. facilitates the subsequent pattern recognition based on the trained model. In some embodiments, windowing techniques (e.g sliding window) and use of machine learning techniques for auto-segmentation may be performed in this step.

The result of the segmentation process in step 603 are individual segments that may have a predefined size or a variable size, and that may or may not overlap. If auto-segmentation is used the characteristics of the signal is used to create segments assumed to include signal properties caused by the same event. For example, referring to FIG. 5, 502 may be such a segment. In step 604 each data frame is subjected to any additional pre-processing and feature extraction.

In step 605 one or more segments and, in some embodiments, already extracted features are used to determine whether the segments include information that may be classified as indicative of a status that warrants logging or issuance of a warning, alert or alarm. This classification may be based on a pattern recognition model that has been created through machine learning as described above. In some embodiments, the classification is not only based on individual segments, but also on combination of segments. For example, a segment may be classified as likely to signify that the patient has fallen, while a subsequent segment may indicate that the patient has got back on their feet, is still on the floor but moving, or is still on the floor and not moving. It should be noted that the pattern recognition primarily works directly on sensor data, not (at least not exclusively) on high level information that has already been extracted from the sensor data. This allows the invention to be trained to detect a wide range of relatively subtle behavior patterns, and not only on high level status changes such as patient entering room, time in bed, time out of bed, etc. High level information obtained by feature extraction from the DSP pre-processing or from one pattern recognition model may be delivered as input to another pattern recognition model, alone or in combination with other data.

A similar sequence of steps may be performed on audio data. A microphone is continuously listening 611 for sounds. Registered sounds are subjected to audio filtering 612, in particular it may be important to suppress background noise. The audio signal may then be subject to segmentation in step 613 in order to create suitable frames of audio data. The frames may be subject to pre-processing and feature extraction 614 before classification is performed in step 615. Again, the classification may be based on machine learning. The feature extraction may include speech recognition.

If additional sensors are present, corresponding processes may be performed for each sensor.

Subsequent to the separate classification of sensor data from respective sensors, the sensor data may be merged in a sensor fusion step 621. Sensor fusion may involve additional pre-processing in order to normalize, scale and resample data in order to combine data from different types of sensors in order to facilitate concurrent processing of fused data. This process creates a fused stream of sensor data that can be subject to processing and classification in step 622. This step is performed in order to obtain enhanced accuracy by taking data from several types of sensors into consideration at the same time. In some embodiments processing and classification is only performed on fused data, in which case steps 605 and 615 are omitted.

The sensor fusion 621 may alternatively only include the results of classification steps for individual sensors and not sensor data as such. For example, the data to be fused may be an indication of a fall from the UWB sensor detected in step 605 and an indication of a shout from the microphone detected in step 615. In some embodiments the sensor fusion 621 includes both pre-processed sensor data and classification results from respective sensors.

The processing in step 622 may confirm classification performed on data from individual sensors, override such classification, or result in classification not obtained from individual sensor data analysis. The result is higher confidence in the correctness of the classification, additional detail in the resulting data, and/or higher accuracy of measurements. The final result of classification is that the system determines that no abnormal behavior is detected, that abnormal behavior is detected and classified as indicative of a specific event or as predicting a specific event, or that abnormal behavior is detected but unknown in the sense that it cannot be associated with any specific event or prediction. The latter is a special case that may be treated as a separate specific event ("something is wrong, but I don't know what it means"). In some embodiments of the invention, even behavior that is not considered abnormal is also classified. Examples include "sleeping", "snoring", "turning in bed" etc. Classification of such events may be utilized for long term tracking of changes in medical condition and for improvement of the trained model.

The result is delivered as output 623 that may be transmitted to health personnel, caregivers, relatives or other relevant persons, or it may be logged for further analysis or future reference.

It should be realized that various embodiments may implement only a subset of the steps shown in FIG. 6. For example, it may not be considered necessary to perform filtering and pre-processing both prior to and subsequent to the segmentation step, at least not for all sensor types.

Furthermore, the drawing illustrates an embodiment where classification is performed on individual sensor data in steps 605 and 615, and again on combined sensor data or combined classifications in steps 621, 622. It will be readily understood that this will not be done in embodiments with only one sensor. In embodiments with several sensors classification may be performed either prior to sensor fusion, subsequent to sensor fusion, or both.

Figure 7:
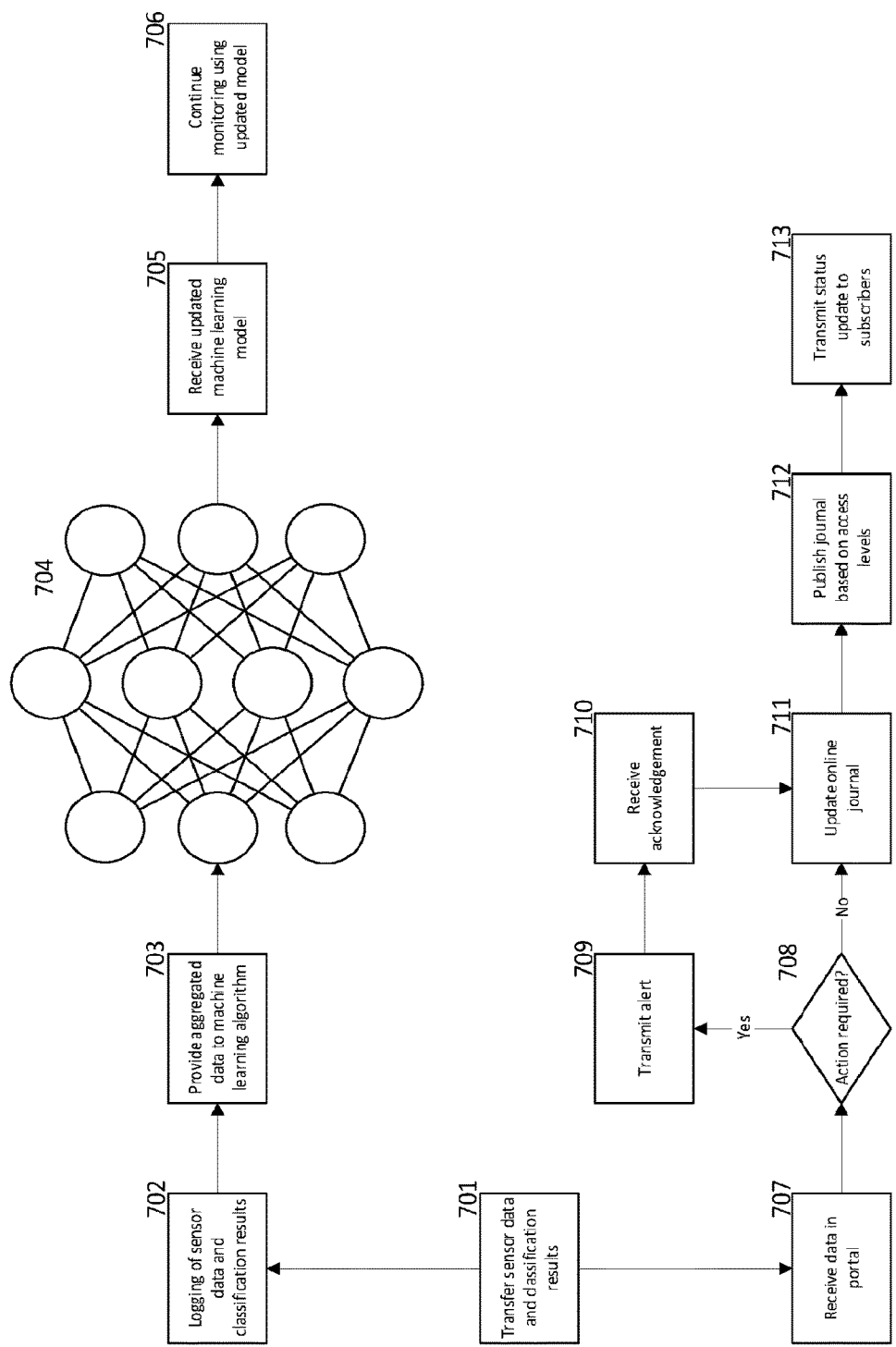
FIG. 7 is a flow chart illustrating machine learning and information distribution in accordance with an embodiment of the invention.

Reference is now made to FIG. 7, which illustrates an exemplary embodiment of the further utilization of data subsequent to the output in step 623. This is illustrated in two branches, one of which represents the further updating of the machine learning model used for classification of sensor data, and one of which represents distribution of the results of the classification to persons that may have a need for this information.

In step 701 sensor data and classification results are transferred to a log 702 and to a portal 707. The log 702 may be part of the local device 11 or it may be part of the cloud service 9. It is, of course, possible to maintain logs both locally and in the cloud. After a sufficient amount of data has been logged in step 702 aggregated data is provided in step 703 to a machine learning algorithm. In step 704 the machine learning algorithm learns from the aggregated data and creates an updated trained model. This updated trained model is received in step 705 such that it may be used in continued monitoring in step 706.

If machine learning is implemented locally on the device 11 using machine learning module 304, the steps described above are performed on the device 11 on a log stored in memory 303. In some embodiments, however, machine learning is provided as a service by the cloud service 9. In that case the transferring step 701 includes transferring data to the cloud service 9, the logging step 702 includes logging data in a database that is part of the cloud service 9, the machine learning is performed in the cloud 9 and the updated model is received by the local device 11 in step 705. It is possible to combine local and cloud based machine learning, for example by maintaining different models for classification of data from different sensors or combination of sensors and updating some models locally and others in the cloud.

Machine learning may be performed on data received by individual sensors as well as on fused sensor data, and based on detection of specific events as well as development of long term trends. The machine learning may be supervised or unsupervised, or a combination of both. Among machine learning algorithms that may be utilized by the system are timeseries analysis, anomaly detection, classification, regression, deep learning algorithms, neural networks and evolutionary neural networks, Bayesian methods, Kalman filters or a combination of such methods. Big data analysis, dimensionality reduction and clustering algorithms may also be applied. It should be noted that for the purposes of the present disclosure and the appended claims, machine learning is intended to include any algorithm that allows the system to maintain a model that enables recognition of patterns associated with events in the received sensor data and to adapt this model based on reception of such sensor data over time.

The second branch in FIG. 7 illustrates how data is received in a portal in step 707. If machine learning is performed in the cloud 9, the transfer of data performed in step 701 to the log in step 702 and the portal in step 707 may be one and the same. However, the transfer to the portal may be separate from logging, because the log is local to the device 11 or because logging and distributing data requires different datasets. The portal can be assumed to be a data distribution service provided by the cloud 9, for example using web technologies as described above.

After data has been received in the portal it is determined in step 708 whether any action by health personnel, caregivers or relatives is required. If not the process proceeds to step 711, but if action is required a notification is transmitted in step 709, for example in the form of an alarm message to an on duty nurse. Such an alarm message may have to be acknowledged by the recipient 710 in order for the system to return to a normal state. Otherwise, the system may be configured to transmit further alarm messages, activate audible alarms or perform other actions.

In step 711 received event classifications and alarms or other notifications are entered in a patient journal. This journal may contain information that can easily be interpreted by relevant personnel, and may include text, graphical representations, measurements and more. The contents of this journal may be made accessible to users of the system based on access rights in step 712. Access rights may be dependent on a user's role relative to the patient, e.g. as doctor, nurse, caregiver, or relative. Information may also be automatically transmitted to subscribers. Subscribers in this context are people with specific roles, or more precisely devices from which people with specific roles have logged in and requested automatic update of certain information, for example by using an app designed for this purpose.

In the present disclosure, the word patient has been used to refer to persons that are monitored by a system according to the invention. The term should not be interpreted to mean that such a person is subject to medical treatment, authority or care of any particular type of health personnel or institution, or that such a person has been given any particular diagnosis. Instead, any person who is not only a user of the system, but also subject to monitoring, even if it is a private person resident in his or her own home.—should be interpreted widely to include any person who may potentially suffer from the kind of events of conditions the system is configured to detect or monitor.

The cloud service 9 may be implemented as one or more server computers or similar devices that provide services accessible from the local device 11. For the purposes of the present disclosure these computers or devices have been referred to collectively as the cloud or cloud services. It should be noted that these services may be distributed between multiple devices which do not have to be co-located and do not have to be operated by the same legal entity. For example, if a number of similar local devices 11 are installed in a nursing home, a local server or hub may provide some functionality in the form of signal processing, pattern recognition or machine learning as well as activation of local alarms. Furthermore, a remotely located server—or several servers—may provide similar functionality, and also provide message distribution, web publishing and other forms of information storage and provision. It is also possible to use commercially available machine learning services in order to retrain or update the pattern recognition model. Finally, all of these options—a local server, a cloud back end, and a commercially available machine-learning platform—may be implemented in the same system, and tasks may be divided between them or replicated over several servers or online services. Consequently, the term cloud service as it is used in the present disclosure and in the claims is intended to include any service performing the described functions on data provided, at least in part, from the local device, whether those services are executed on a locally installed server or hub or on one or more servers accessible over wide area networks.

The flexibility of the present invention with respect to selection of sensor types, inclusion of manually entered information, as well as inclusion of data from third party sensors (e.g. wearables) and even external data such as weather, humidity, time of day, time light has been on in a room, time television has been on in a room, etc. enables training of the pattern recognition model (or models) to a wide range of conditions and events that it has not previously been possible to monitor and detect.

For example, by logging personal information manually it may be possible to correlate sensor data and such information as medication (including changes in or missed), amount of physical activity, sleep pattern and quality (measured or experienced), time to bed, stress, emotional states, intake of alcohol, intake of caffeine, sensory over stimulation (stroboscopic light, other flashing light, computer or TV screens, repetitive sounds, noise), hormonal changes, diet changes, allergies, physical or psychological distress or trauma with onset of epileptic seizures, other seizures, insomnia, depression, etc. This makes it possible to identify triggers of undesirable events or conditions, to update the pattern recognition model to monitor for such triggers, and to issue alarms or advice when behavior indicates increased risk of the onset of an undesirable event or condition.

The combination of UWB with sound is believed to be particularly useful for detection or prediction of certain events because sound carries information that is not readily detected by other sensors. Such information may relate to strained breathing, snoring, stridor, wheezing, which may indicate breathing related problems, as well as cries, screams, other sounds that indicate distress, crying, etc. This also includes sounds that may be specific to e.g. an epileptic seizure, other seizures, or other medical conditions. Combination of movement and sound in sensor fusion provides abilities that has not been available through prior systems.

The ability to combine several types of data from different types of sources, and the invention's ability to train based on individual behavior will reduce the number of false alarms and may thereby prevent alarm fatigue among health personnel.

The ability to not only detect abnormal behavior, but also track and learn based on normal behavior makes it possible to detect secondary events or needs, i.e. situations that are not critical, but that still require attention. For example, detecting that a patient has been laying in a specific position for a certain amount of time may alert caregivers that the patient needs to be turned in bed in order not to develop pressure ulcers (bedsores, or pressure injuries). This can be done since the system may detect posture in bed, movement in bed, and, as a result of the individual machine learning, adaptation of the pattern recognition to the patient's history of developing pressure ulcers.

Registration of manual entries may be done from any device capable of communicating with the cloud service 9 and with the necessary access rights. This means that the patients themselves may enter some information, other information may be updated by relatives or caregivers, while some information may only be entered or updated by health personnel.

The present invention may be provided in the form of a system including several devices installed at respective locations, and one or more local and/or remote server computers collectively referred to as a cloud service.

The invention claimed is:

1. Method of detecting undesirable events or conditions in a patient, comprising:
   transmitting a UWB radar signal from a UWB radar configured to monitor an environment occupied by the patient;
   receiving as a first input signal, a reflected return signal which has been changed relative to the transmitted signal or where time difference between the transmitted and the received signal has been changed by the patient's motion;
   from the received first input signal, deriving data representative of the patient's motion from said changes in the reflected return signal; and
   processing data derived from said first input signal using a pattern recognition model to detect and classify patterns in said data derived from said first input signal as indicative or predictive of one of a plurality of undesirable events or conditions involving said patient.

2. Method according to claim 1, further comprising issuing an alarm when a pattern is classified as indicative or predictive of an undesirable event or condition in said patient.

3. Method according to claim 1, wherein said movement includes movement of the patient's heart and chest, and the first input signal includes information representative of said patient's vital signs.

4. Method according to claim 1, wherein
   said pattern recognition model is a trained model enabling detection of abnormal behavior based on a reflected return signal from a UWB radar.

5. Method according to claim 4, wherein said trained model is specifically trained to enable detection of at least one of an onset of an epileptic seizure and a fall.

6. Method according to claim 1, further comprising:
   receiving a second input signal from at least one additional sensor; and
   performing sensor fusion on the first and the second input signal or on information derived from the first and the second input signal.

7. Method according to claim 6, wherein
   sensor fusion is performed prior to classification, and the fused result is the data derived from said first input signal and processed using the pattern recognition module.

8. Method according to claim 6, further comprising:
   performing classification of patterns in data derived from the second input signal,
   wherein sensor fusion is performed subsequent to classification, and
   the fused result is used to confirm, override, or provide different classification results than the classification results provided from classification of patterns in the respective signals.

9. Method according to claim 6, wherein said at least one additional sensor is chosen from the group consisting of: a microphone, a thermometer, a photodetector, an air quality sensor, an air humidity sensor, VOC-sensor, a barometer, and a heart rate sensor.

10. Method according to claim 1, wherein said receiving and processing using a pattern recognition model is performed in a local device containing or connected to said UWB radar.

11. Method according to claim 1, wherein said information representative of the patient's motion includes information representative of random body movement.

12. Method according to claim 1, further comprising:

upon detecting and classifying a pattern indicative or predictive of one of a plurality of undesirable events or conditions:

classifying said detected pattern as indicative of a specific event or prediction;

selecting a message to be representative of or associated with said alarm based on the result of said classifying; and transmitting or publishing said message to an intended recipient.

13. A device for monitoring a patient in order to detect undesirable events or conditions, comprising:

a processor configured to receive sensor data including a first input signal which is a reflected return signal from an UWB radar which has been changed relative to a transmitted radar signal or where time difference between the transmitted and the received radar signal has been changed by the patient's motion, and to derive data representative of the patient's motion from said changes in the first input signal;

a memory;

a pattern recognition model stored in said memory and enabling said processor to perform pattern recognition processing of the data derived from said first input signal and to detect and classify patterns in said data derived from said first input signal as indicative or predictive of an undesirable event or condition in a patient within a field of view of said UWB radar.

14. A device according to claim 13, further comprising:
a communication interface,
wherein said processor is further configured to:
transmit an alarm message over said communication interface when a pattern is classified as indicative or predictive of an undesirable event or condition in said patient.

15. A device according to claim 13, wherein
said pattern recognition model is a trained model enabling detection of abnormal behavior based on a reflected return signal from an UWB radar.

16. A device according to claim 15, wherein
said trained model is trained to enable detection of at least one of an onset of an epileptic seizure and a fall.

17. A device according to claim 13, wherein the processor is further configured to:
receive a second input signal from at least one additional sensor; and
perform sensor fusion on the first and the second input signal or on information derived from the first and the second input signal.

18. A device according to claim 17, wherein the processor is further configured to perform sensor fusion prior to classification, and the fused result is the data derived from said first input signal and processed using the pattern recognition module.

19. A device according to claim 17, wherein the processor is further configured to:
perform classification of patterns in data derived from the second input signal;
perform sensor fusion subsequent to classification; and
use the fused result to confirm, override, or provide different classification results than the classification results provided from classification of patterns in the respective signals.

20. A device according to claim 13, further comprising said UWB radar as a component.

* * * * *